US012600935B2

(12) United States Patent
Kang et al.

(10) Patent No.: US 12,600,935 B2
(45) Date of Patent: Apr. 14, 2026

(54) DEVICE FOR FORMING AND COUNTING SPHEROIDS AND METHOD FOR PRODUCING SAME, AND SPHEROID CULTURING METHOD AND COUNTING METHOD USING SAME

(71) Applicants: KOREA RESEARCH INSTITUTE OF CHEMICAL TECHNOLOGY, Daejeon (KR); THE INDUSTRY & ACADEMIC COOPERATION IN CHUNGNAM NATIONAL UNIVERSITY (IAC), Daejeon (KR)

(72) Inventors: Sun Woong Kang, Daejeon (KR); Kang Moo Huh, Daejeon (KR); Sung Hwan Moon, Seoul (KR); Da Eun Kim, Daejeon (KR); Hye Min Oh, Daejeon (KR); Hye Eun Shim, Daejeon (KR)

(73) Assignees: KOREA RESEARCH INSTITUTE OF CHEMICAL TECHNOLOGY, Daejeon (KR); THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 522 days.

(21) Appl. No.: 16/760,583

(22) PCT Filed: Oct. 25, 2018

(86) PCT No.: PCT/KR2018/012682
§ 371 (c)(1),
(2) Date: Apr. 30, 2020

(87) PCT Pub. No.: WO2019/088560
PCT Pub. Date: May 9, 2019

(65) Prior Publication Data
US 2020/0263122 A1 Aug. 20, 2020

(30) Foreign Application Priority Data
Nov. 3, 2017 (KR) ........................ 10-2017-0145791

(51) Int. Cl.
*C12M 1/34* (2006.01)
*C12M 1/00* (2006.01)
(Continued)

(52) U.S. Cl.
CPC ............ *C12M 41/36* (2013.01); *C12M 23/20* (2013.01); *C12M 23/22* (2013.01); *C12M 25/02* (2013.01); *C12Q 1/06* (2013.01)

(58) Field of Classification Search
CPC ...... C12M 41/36; C12M 23/20; C12M 23/22; C12M 25/02; C12Q 1/06
(Continued)

(56) References Cited

U.S. PATENT DOCUMENTS 5,759,494 A * 6/1998 Szlosek .................. G01N 21/03
422/553
7,727,759 B2 * 6/2010 Ozawa ................. C12N 5/0075
435/305.2
(Continued)

FOREIGN PATENT DOCUMENTS

JP 2015-73520 A 4/2015
KR 10-2009-0004879 A 2/2014
(Continued)

OTHER PUBLICATIONS

Piedmont Plastics, Top Types of Flexible Plastic Sheet, Accessed Apr. 18, 2024, Available online at: www.piedmontplastics. com/ blog/flexible-plastic-sheet-top-choices.*
(Continued)

*Primary Examiner* — Jennifer M.H. Tichy
(74) *Attorney, Agent, or Firm* — RAPHAEL BELLUM PLLC

(57) ABSTRACT

A device for forming and counting spheroids according to one embodiment of the present invention may comprise a substrate, and a mesh member which is configured to be able to be positioned on the surface of the substrate and has a
(Continued)

(a)                    (b)                    (c)

plurality of protruding members. The plurality of protruding members intersects one another in the form of a mesh so as to form a plurality of pores.

9 Claims, 5 Drawing Sheets

(51) Int. Cl.
    *C12M 1/12*           (2006.01)
    *C12Q 1/06*           (2006.01)

(58) Field of Classification Search
    USPC ........................................................... 435/39
    See application file for complete search history.

(56)                 References Cited

U.S. PATENT DOCUMENTS

2007/0168021 A1*   7/2007   Holmes, Jr. .............. A61L 27/38
                                                         435/399

2014/0322806 A1*   10/2014   Bennett .................. C12M 29/04
                                                         435/325
2017/0275586 A1*   9/2017   Huh ....................... C12M 23/10

FOREIGN PATENT DOCUMENTS

| | | |
|---|---|---|
| KR | 10-1362293 | 2/2014 |
| KR | 10-2014-0069148 A | 6/2014 |
| KR | 10-1437147 B1 | 9/2014 |
| KR | 10-2016-0027669 A | 3/2016 |

OTHER PUBLICATIONS

Cho, M. O. et al., "Bioinspired Tuning of Glycol Chitosan for 3D Cell Culture", NPG Asia Materials, 2016, vol. 8, e309, inner pp. 1-10, <DOI:10.1038/am.2016.130> See abstract: p. 2, right column, "Preparation of Culture Plates Coated with GC and HGC" section.

* cited by examiner (a)                    (b)                    (c)

DEVICE FOR FORMING AND COUNTING SPHEROIDS AND METHOD FOR PRODUCING SAME, AND SPHEROID CULTURING METHOD AND COUNTING METHOD USING SAME

TECHNICAL FIELD

The present invention relates to a device for forming and counting spheroids capable of forming spheroids in a uniform size and counting them, and a spheroid culturing method and counting method using the same.

BACKGROUND

Cells and tissues in the body grow, differentiate, and develop while interacting with one another in a complex three-dimensional structure. But most cell culture is carried out in a two-dimensional, impermeable flat surface. Accordingly, the two-dimensional cell culture has a limitation of the inability to simulate the environmental conditions of cells in our body. Recently, the culture of spheroids, which are three-dimensional cell tissues having an equivalent function as in vivo, are receiving attention. Since a method of transplanting aggregated cells or other methods are used in transplanting Langerhans islet cells to induce normal secretion of insulin for the treatment of diabetes, mass production of spheroids is required. In addition, with the maturation of stem cell research, several methods have been attempted to culture stem cells in three dimensions and to apply them to studies of various differentiation mechanisms. Conventional three-dimensional (3D) cell culture methods include a hanging-drop method, a rotary culture method, a centrifugal separation method, a micromolding method, and so on. However, such conventional culture methods have a limit to culturing spheroids of uniform size.

Furthermore, there has been a need for a device for counting such spheroids more conveniently and accurately, but no such a device exists to date.

SUMMARY OF INVENTION

Technical Objects

It is an object of the present invention to solve the issues discussed above and other problems associated therewith.

It is an exemplary object of the present invention to provide a device for culturing spheroids of uniform size.

It is another exemplary object of the present invention to provide a device for counting spheroids more conveniently and accurately.

Technical Solution

A device for forming and counting spheroids in accordance with an embodiment of the present invention may comprise a substrate; and a mesh member configured to be positionable on a surface of the substrate and having a plurality of protruding members.

In an embodiment, the plurality of protruding members may intersect one another in the form of a mesh so as to form a plurality of pores.

In an embodiment, the mesh member may be coated with hexanoyl glycol chitosan.

In an embodiment, the pores may have a width of 50 to 500 μm.

In an embodiment, the surface of the substrate may be coated with hexanoyl glycol chitosan.

In an embodiment, the substrate may be a slide glass.

In an embodiment, when the mesh member is placed on the surface of the substrate, one face of the mesh member on which the protruding members are not formed may be in contact with the surface of the substrate.

In an embodiment, the mesh member and the substrate may be coupled to each other by an assembly member.

In an embodiment, the protruding members may comprise a plurality of first protruding members extending in a first direction and spaced apart from one another, and a plurality of second protruding members extending in a second direction intersecting with the first direction and spaced apart from one another.

A method for manufacturing a device for forming and counting spheroids in accordance with an embodiment of the present invention may comprise: a solution preparation step of preparing a hexanoyl glycol chitosan solution; a substrate coating step of coating a substrate by spraying the prepared solution onto the substrate, followed by drying the substrate; a mesh member coating step of coating a mesh member by spraying the prepared solution onto the mesh member, followed by drying the mesh member, and a step of assembling the coated substrate and the mesh member using an assembly member.

In an embodiment, in the mesh member coating step, the mesh member may be sprayed with the prepared solution while the mesh member is in a state of being erected and fixed.

In an embodiment, the hexanoyl glycol chitosan solution may be of 0.01 to 1 wt %.

A method for culturing spheroids using a device for forming and counting spheroids in accordance with an embodiment of the present invention may comprise: seeding a plurality of cells in the device; and obtaining spheroids observed in each pore of the device after several days.

A method for counting spheroids using a device for forming and counting spheroids in accordance with an embodiment of the present invention may comprise: seeding spheroids in the device; positioning the spheroids into each pore of the device by shaking the device in both directions parallel to one face of the device; placing the device on a stage of a microscope; and counting the spheroids in a field of view by moving a position on an image in the microscope.

Effects of the Invention

If a device for forming and counting spheroids in accordance with an embodiment of the present invention is used, spheroids can be mass-cultured in a uniform size without any special equipment or additional processes and accordingly, it can be expected to be used in industries of various fields such as regenerative medicine, artificial organs, production of useful biomaterials, new drug screening, animal substitute test methods, and so on.

In addition, since the device for forming and counting spheroids in accordance with an embodiment of the present invention is coated with hexanoyl glycol chitosan (HGC) and thus minimizes the adhesion to a surface of a culture medium, there is an advantage that 3D spheroids can be easily recovered after culturing them.

Furthermore, as it is possible to place and then use the device for forming and counting spheroids in accordance with an embodiment of the present invention on an existing container in order to count the spheroids, there is no need to provide a separate counting device, and accordingly, the cost is reduced and it is very convenient to use.

On the other hand, the effects described above are merely exemplary, and other effects anticipated or expected from the detailed configuration of the present invention from the perspective of those skilled in the art may also be added to the unique effects of the present invention.

DETAILED DESCRIPTION OF EMBODIMENTS

Figure 1:
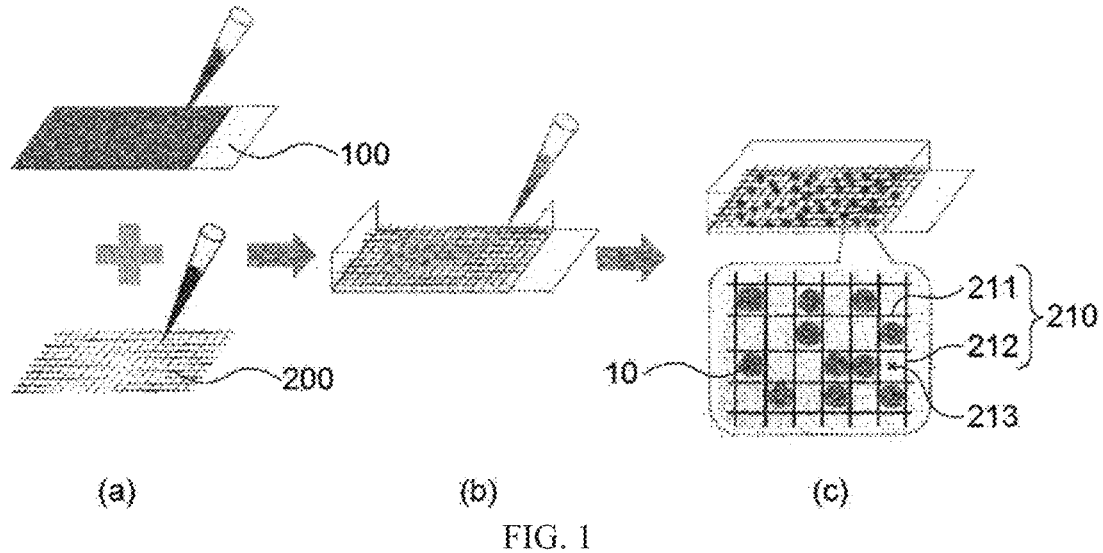
FIG. 1 is a diagram for generally describing a device for forming and counting spheroids in accordance with an embodiment of the present invention.

Hereinafter, embodiments disclosed herein will be described in detail with reference to the accompanying drawings, and like reference numerals will be assigned to like or similar components throughout the drawings and repetitive description will be omitted for purposes of clarity. The terms "module" and "part" added to the components used in the following description are given or used only for ease of drafting the specification, and do not have meanings or roles distinguished from each other in themselves. Moreover, in describing the embodiments disclosed herein, if it is determined that detailed descriptions of related known art may obscure the subject matter of the embodiments disclosed herein, such detailed descriptions will be omitted. In addition, it should be understood that the accompanying drawings are only for easy understanding of the embodiments disclosed herein and the technical spirit disclosed herein is not limited by the accompanying drawings, and all modifications, equivalents, or substitutes within the spirit and technical scope of the present invention are to fall within the present invention.

Although terms including ordinal numbers such as first, second, and so on may be used to describe various components, these components are not limited by such terms. Such terms are used only for the purpose of distinguishing one component from another.

When one component is said to be "coupled" or "connected" to another component, it is to be understood that although the one component may be directly coupled with or connected to that another component, other components may also exist in-between. On the other hand, when one component is said to be "directly coupled" or "directly connected" to another component, it should be understood that no other component exists in-between.

Singular expressions include plural expressions unless expressly indicated otherwise in the context.

In the present application, it should be understood that the terms "comprise" or "have" are intended to indicate the existence of features, numbers, steps, operations, components, parts, or combinations thereof described in the specification, and are not intended to preclude the existence or possibility of addition of one or more other features, numbers, steps, operations, components, parts, or combinations thereof.

Hereinafter, a device for forming and counting spheroids in accordance with an embodiment of the present invention will be described with reference to the drawings.

FIG. 1 is a diagram for generally describing a device for forming and counting spheroids in accordance with an embodiment of the present invention.

The device for forming and counting spheroids in accordance with an embodiment of the present invention may comprise a substrate 100 and a mesh member 200.

The substrate 100 may be made of a light transmissive material. For example, the substrate 100 may be a slide glass.

The mesh member 200 may be configured to be positionable on a surface of the substrate 100.

For example, the mesh member 200 may be made of a flexible material and may be made to cover the surface of the substrate 100 in an unfolded state.

Further, the mesh member 200 may have a plurality of protruding members 210. The plurality of protruding members 210 may intersect one another in the form of a mesh so as to form a plurality of pores 213.

Specifically, the protruding members 210 may comprise a plurality of first protruding members 211 extending in a first direction and spaced apart from one another and a plurality of second protruding members 212 extending in a second direction intersecting with the first direction and spaced apart from one another. The plurality of first protruding members 211 may be parallel to one another, and likewise, the plurality of second protruding members 212 may be parallel to one another.

Meanwhile, the plurality of pores 213 may be sized such that each pore 213 is suitable for accommodating one spheroid 10. For example, the pores 213 may have a width of 50 to 500 μm, more preferably of about 140 μm. If the pores 213 have a width of 140 μm, spheroids may be cultured in a size that can be most suitably used in various cell experiments.

More specifically, one face of the mesh member 200 may not have the protruding members 210 formed thereon, and the other face thereof may have the protruding members 210 formed thereon. In this case, when the mesh member 200 is placed on the surface of the substrate 100, the one face of the mesh member 200 on which the protruding members 210 are not formed may be positioned to be in contact with the surface of the substrate 100.

The substrate 100 and the mesh member 200 stacked as such may be coupled or fixed to each other by a separate assembly member.

Meanwhile, the device for forming and counting spheroids in accordance with an embodiment of the present invention may be coated with hexanoyl glycol chitosan (HGC) on its inner surface.

More specifically, the substrate 100 and the mesh member 200 of the device for forming and counting spheroids may each be coated with hexanoyl glycol chitosan.

In the following, a method for manufacturing a device for forming and counting spheroids in accordance with an embodiment of the present invention will be described in detail with reference to the drawings.

Figure 2:
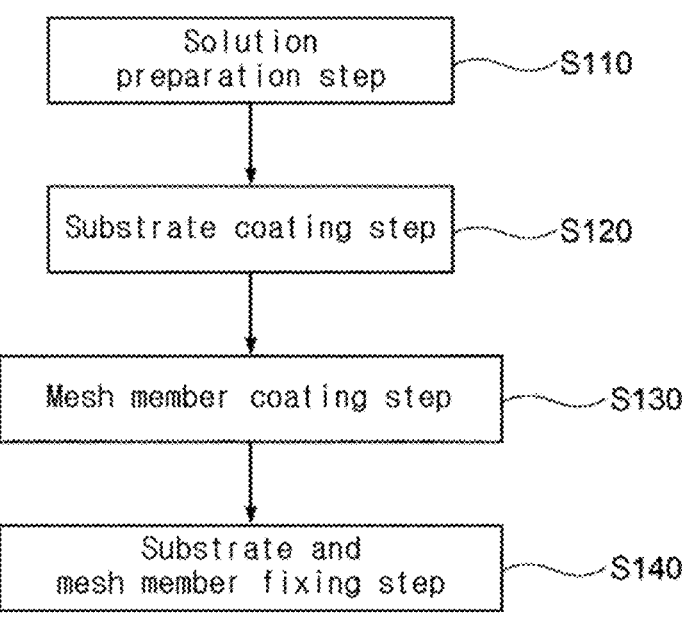
FIG. 2 is a flow diagram of a method for manufacturing a device for forming and counting spheroids in accordance with an embodiment of the present invention.
Figure 3:
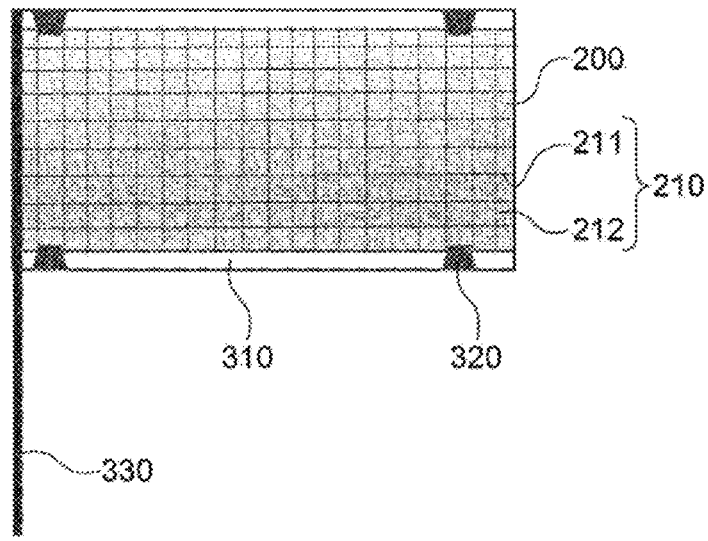
FIGS. 3 and 4 are diagrams for illustrating a method for manufacturing a device for forming and counting spheroids in accordance with an embodiment of the present invention.
Figure 4:
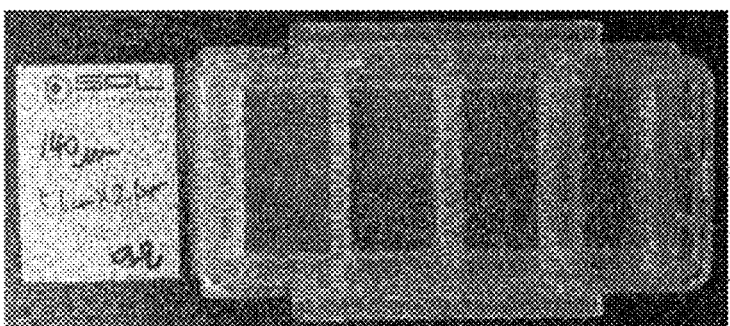

FIG. 2 is a flow diagram of a method for manufacturing a device for forming and counting spheroids in accordance with an embodiment of the present invention. FIGS. 3 and 4 are diagrams for illustrating a method for manufacturing a device for forming and counting spheroids in accordance with an embodiment of the present invention.

The method for manufacturing a device for forming and counting spheroids in accordance with an embodiment of the present invention may comprise a solution preparation step S110, a substrate coating step S120, a mesh member coating step S130, and a substrate and mesh member fixing step S140.

In the solution preparation step S110, a hexanoyl glycol chitosan (HGC) solution is prepared. In one embodiment, the HGC solution was prepared as follows.

Distilled water (DW) treated with pressurized sterilization was filtered through a 0.2 μm filter, so as to carry out a process of removing bacteria and the like. A quantity of 20 ml of the treated distilled water was transferred to a 50-ml tube, and then 0.1 g of measured HGC was added to the tube. The distilled water containing the HGC therein was vortexed for 1 to 2 minutes once every hour while being kept refrigerated (at 4° C.). It took about 3 to 4 days for the HGC to be completely dissolved and to turn into an HGC solution.

At this time, the concentration of the HGC solution may be 0.01 to 1 wt %, preferably about 0.5 wt %.

Next, in the substrate coating step S120, the substrate 100 is coated by spraying the prepared HGC solution onto the substrate 100, followed by drying the substrate 100.

A substrate (or slide glass) 100 coating process in accordance with an embodiment is as follows. After removing the needle part of a 1-ml syringe, a quantity of 400 ml of HGC solution was taken. The HGC solution of 400 ml that was measured earlier was sprinkled evenly on the slide glass (of 5.6 cm×2.6 cm). The slide glass after completing the above process was dried in an oven at 55° C. for about one day.

Next, in the mesh member coating step S130, the mesh member 200 is coated by spraying the prepared HGC solution onto the mesh member 200, followed by drying the mesh member 200.

In the mesh member coating step S130, the mesh member 200 may be sprayed with the prepared solution while the mesh member 200 is in a state of being erected and fixed.

The mesh member may be erected and fixed using a fixation frame, as shown in FIG. 3. Specifically, the fixation frame 300 may comprise a main body 310, a fixing part 320, and a fixing bar 330. The mesh member 200 may be fixed to the main body 310 by means of the fixing part 320. The main body 310 may be positioned spaced apart from the ground by the fixing bar 330. Meanwhile, the fixation frame 300 may be an iron drying frame.

At this time, the reason the mesh member 200 is erected and fixed is to prevent the pores 213 of the mesh member 200 from being blocked by the HGC solution (coating solution) when coating the mesh member 200.

Next, the HGC solution is evenly sprinkled onto the fixed mesh member 200 using a 1 ml pipette.

The mesh member 200 after completing the above process is dried in a clean laboratory bench for a day while being erected and fixed.

In the substrate and mesh member fixing step S140, the coated substrate 100 and mesh member 200 may be assembled using an assembly member.

For example, the mesh member 200 that had completed the coating process was cut into a size of 5.6 cm×2.6 cm and then placed on the slide glass that had completed the coating process. As shown in FIG. 4, they were fixed using a fixing member. The fixing member may be a clip.

In the following, a method for culturing spheroids using a device for forming and counting spheroids produced as above will be described with reference to the drawings.

Figure 5:
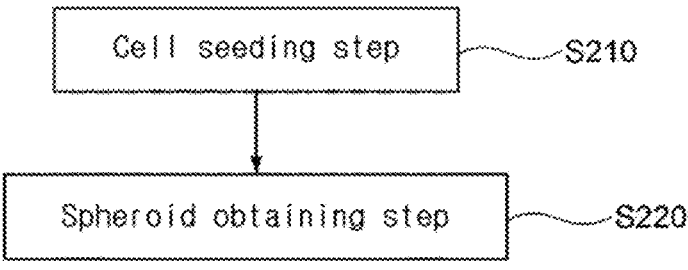
FIG. 5 is a flow diagram of a method for culturing spheroids using a device for forming and counting spheroids in accordance with an embodiment of the present invention.

FIG. 5 is a flow diagram of a method for culturing spheroids using a device for forming and counting spheroids in accordance with an embodiment of the present invention. FIGS. 6 to 9 are diagrams for illustrating a method for culturing spheroids using a device for forming and counting spheroids in accordance with an embodiment of the present invention;

The method for culturing spheroids using a device for forming and counting spheroids in accordance with an embodiment of the present invention may comprise a cell seeding step S210 and a spheroid obtaining step S220.

In the cell seeding step S210, a plurality of cells are seeded in the device for forming and counting spheroids.

In one embodiment, liver cancer cells of $1 \times 10^5$ cells/1 ml were seeded into one well of a 4-well cell culture slide (pore size: 140 μm).

Figure 6:
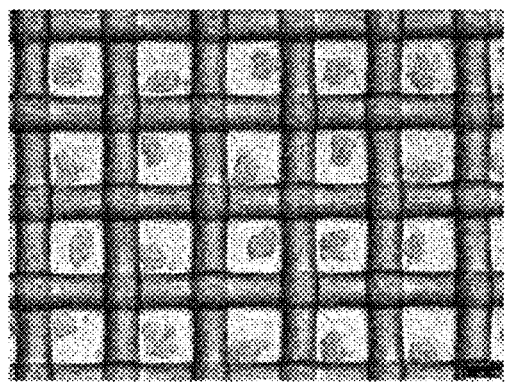
FIGS. 6 to 9 are diagrams for illustrating a method for culturing spheroids using a device for forming and counting spheroids in accordance with an embodiment of the present invention.
Figure 7:
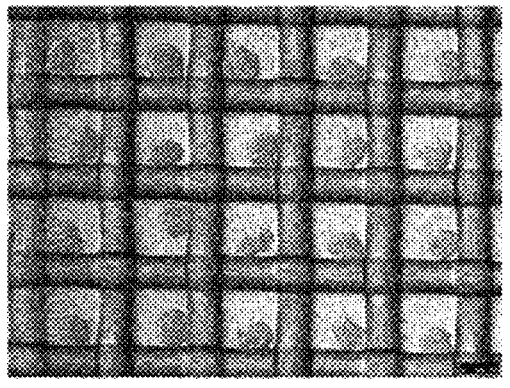

As shown in FIG. 6, cells aggregate in a similar size in the lattice after one day from the cell inoculation. After two days from the cell inoculation, densely aggregated spheroids can be observed as shown in FIG. 7.

In the spheroid obtaining step S220, several days later, spheroids observed in respective pores 213 of the device are obtained.

Figure 8:
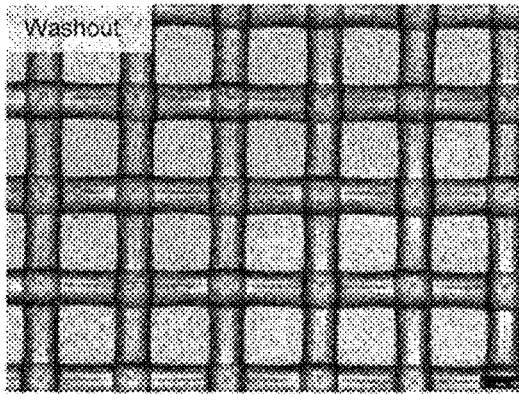
Figure 9:
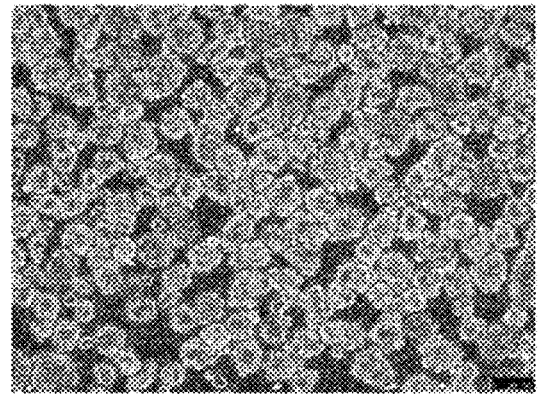

In one embodiment, the end of the tip is cut when obtaining spheroids, and spheroids can be obtained through a washout process. FIG. 8 shows the mesh member 200 after the spheroids were obtained through the washout process, and FIG. 9 shows a picture of the obtained spheroids.

Meanwhile, accurate counting is required in order to use cell-spheroids produced in a uniform size for experiments. In the following, an improved method for counting spheroids compared with the conventional method will be described with reference to the drawings by using the device for forming and counting spheroids that is coated with the HGC.

Figure 10:
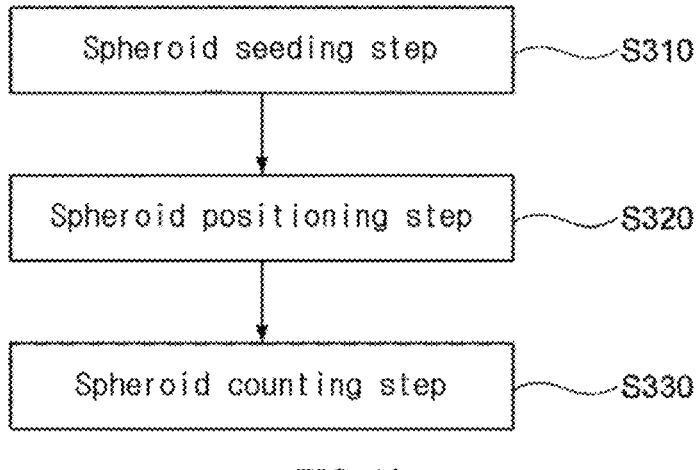
FIG. 10 is a flow diagram of a method for counting spheroids using a device for forming and counting spheroids in accordance with an embodiment of the present invention.
Figure 11A:
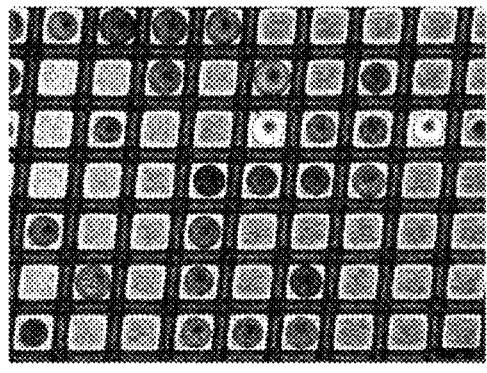
FIGS. 11 and 12 are diagrams for illustrating a method for counting spheroids using a device for forming and counting spheroids in accordance with an embodiment of the present invention.
Figure 11B:
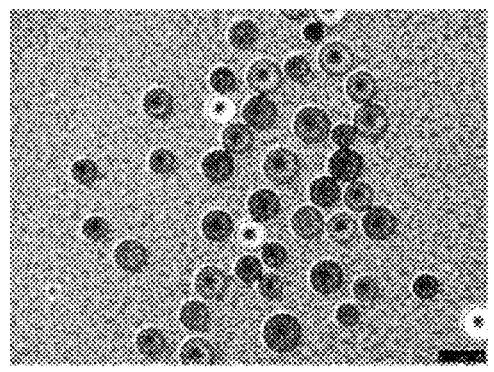
Figure 12:
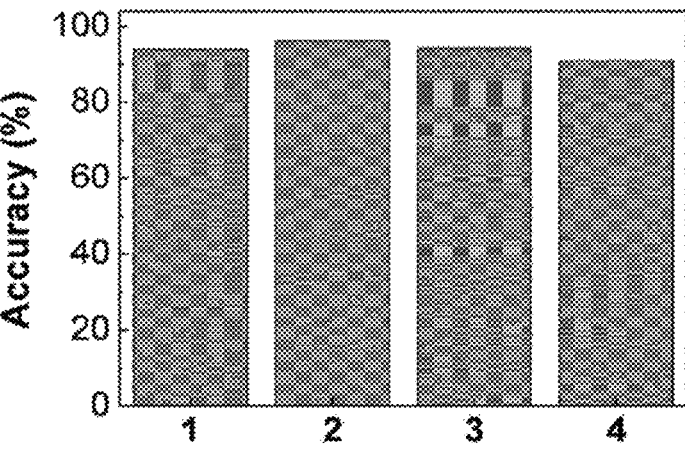

FIG. 10 is a flow diagram of a method for counting spheroids using a device for forming and counting spheroids in accordance with an embodiment of the present invention, and FIGS. 11 and 12 are diagrams for illustrating a method for counting spheroids using a device for forming and counting spheroids in accordance with an embodiment of the present invention.

The method for counting spheroids using a device for forming and counting spheroids in accordance with an embodiment of the present invention may comprise a spheroid seeding step S310, a spheroid positioning step S320, and a spheroid counting step S330.

In the spheroid seeding step S310, the spheroids are seeded in the device for forming and counting spheroids (see (b) of FIG. 1).

In the spheroid positioning step S320, the device is shaken in both directions parallel to one face of the device to position the spheroids into the respective pores 213 of the device (see (c) of FIG. 1).

At this time, the process of shaking the device in both directions may be performed manually or automatically. For example, the device may be connected to a separate drive that reciprocates the device.

Next, the device is placed on the stage of a microscope, and then, the position on the image in the microscope can be moved around to change the field of view.

In the spheroid counting step S330, the spheroids in the field of view may be counted. For example, counting the spheroids can be done manually or automatically. For example, if counting the spheroids is automatically performed, a separate control unit may extract the image of spheroids from the image within the field of view, thereby automatically counting the number of spheroids.

In the following, an experimental example of a method of counting the spheroids will be described.

Referring to FIG. 11, Cytodex microcarriers stained with trypan blue were used instead of cell-spheroids to enhance visibility. The diameter of Cytodex may be 165 to 220 μm.

After dropping 20 μl of a trypan-blue reagent into 5 ml of D-PBS, Cytodex was mixed. After staining for about 20 minutes, samples were prepared by washing out with fresh D-PBS.

The device for counting spheroids coated with HGC is wetted sufficiently with D-PBS or a medium in advance. The mesh size used here may be about 200 μm.

A pipette is used to obtain 100 μl of D-PBS containing Cytodex therein and to seed it in the device for counting spheroids coated with the HGC. The device is shaken well so that one Cytodex can get into one mesh blank (pore) 213. Wait for about 5 minutes for Cytodex to sufficiently settle down to the bottom.

Cytodex present in the mesh was counted while moving the position on the image in the optical microscope around.

As shown in (a) of FIG. 11, the total number of Cytodex was calculated after taking partial photos several times and counting Cytodex. For example, if the count values for photo 1, photo 2, photo 3, photo 4, and photo 5 are 26, 30, 31, 22, and 23, respectively, then the average count value is 26.4. In this case, the number of mesh holes in each photo is 63, and the number of mesh holes for the entire device is 2380. Therefore, the total number of Cytodex can be calculated as 26.4×2380/63=997.

Referring to (b) of FIG. 11, after the counting, the entire Cytodex present in the mesh was counted and then obtained while moving the position on the image in the optical microscope around, and was transferred to a new Petri dish and obtained.

Counting was carried out a total of four times in the same manner as described above. As shown in FIG. 12, the accuracy was confirmed to be over 94%.

Although the invention has been described in detail in connection with only a limited number of embodiments, it should be readily understood that the invention is not limited to such disclosed embodiments. Rather, the invention may be modified to incorporate any number of modifications, alterations, replacements, or equivalent arrangements that have not been described above but correspond to the spirit and scope of the invention. Additionally, while various embodiments of the invention have been described, it should be understood that aspects of the invention may include only some of the described embodiments. Accordingly, the invention should not be considered as being limited by the foregoing description, but is limited only by the scope of the appended claims.

REFERENCE NUMERALS

100: Substrate
200: Mesh member
210: Protruding members
211: First protruding members
212: Second protruding members
213: Pores
300: Fixation frame
310: Main body
320: Fixing part
330: Fixed bar

What is claimed is:

1. A device for forming and counting spheroids, comprising:

a flat substrate; and a flexible mesh member, configured with a plurality of protruding members intersecting parallel to each other in a mesh configuration to form a plurality of pores, wherein the substrate and the mesh member are each coated with hexanoyl glycol chitosan;

wherein each pore is configured to have a flat bottom surface and a suitable size to accommodate one spheroid of uniform size;

wherein the mesh member is fixed by an assembly member positioned at the side of the substrate to place the mesh member in a position above the surface of the substrate and to provide a gap between the mesh member and the surface of the substrate; and wherein the gap between the mesh member and the surface of the substrate is smaller than the size of the spheroid.

2. The device for forming and counting spheroids according to claim 1, wherein the pores have a width of 50 to 500 μm.

3. The device for forming and counting spheroids according to claim 1, wherein the substrate is a slide glass.

4. The device for forming and counting spheroids according to claim 1, wherein the protruding members comprise:

a plurality of first protruding members extending in a first direction and spaced apart from one another; and a plurality of second protruding members extending in a second direction intersecting with the first direction and spaced apart from one another.

5. A method for manufacturing the device for forming and counting spheroids according to claim 1, comprising:

a solution preparation step of preparing a hexanoyl glycol chitosan solution;

a substrate coating step of coating the substrate by spraying the prepared solution onto the substrate, followed by drying the substrate;

a mesh member coating step of coating the mesh member by spraying the prepared solution onto the mesh member, followed by drying the mesh member, and a step of assembling the coated substrate and the mesh member using the assembly member.

6. The method for manufacturing the device for forming and counting spheroids according to claim 5, wherein in the mesh member coating step, the mesh member is sprayed with the prepared solution while the mesh member is in a state of being erected and fixed.

7. The method for manufacturing the device for forming and counting spheroids according to claim 5, wherein the hexanoyl glycol chitosan solution has a concentration of 0.01 to 1 wt %.

8. A method for culturing spheroids using the device for forming and counting spheroids according to claim 1 comprising:

seeding a plurality of cells in the device; and obtaining spheroids in each pore of the device after several days.

9. A method for counting spheroids using the device for forming and counting spheroids according to claim 1 comprising:

seeding spheroids in the device, positioning the spheroids into each pore of the device by shaking the device in both directions parallel to one face of the device;

placing the device on a stage of a microscope; and counting the spheroids in a field of view by moving a position on an image in the microscope.

\* \* \* \* \*